United States Patent [19]

Bonnell et al.

[11] Patent Number: 5,833,596
[45] Date of Patent: Nov. 10, 1998

[54] ENDOSCOPE FOR IMAGING INFRARED EMISSIONS WITHIN THE RANGE OF 2 TO 14 MICRONS

[75] Inventors: Leonard J. Bonnell, Huntingdon Valley, Pa.; Dennis C. Leiner, Jaffrey, N.H.; Thomas Brukilacchio, Reading, Mass.

[73] Assignee: Vipera Systems, Inc., Huntingdon Valley, Pa.

[21] Appl. No.: 631,579

[22] Filed: Apr. 12, 1996

Related U.S. Application Data

[63] Continuation-in-part of Ser. No. 421,949, Apr. 14, 1995, Pat. No. 5,711,755.

[51] Int. Cl.$^6$ ........................................ A61B 1/04
[52] U.S. Cl. ..................... 600/109; 600/473; 359/356; 250/353
[58] Field of Search ........................ 600/109, 160, 600/181, 407, 310, 473, 474; 359/355–357, 350, 360, 894; 356/51; 250/330–334, 352; 348/164

[56] References Cited

U.S. PATENT DOCUMENTS

| | | |
|---|---|---|
| 4,122,853 | 10/1978 | Smith . |
| 4,418,689 | 12/1983 | Kanazawa . |
| 4,783,593 | 11/1988 | Noble . |
| 4,786,813 | 11/1988 | Svenberg et al. . |
| 4,820,923 | 4/1989 | Wellman . |
| 4,872,458 | 10/1989 | Kanehira et al. . |
| 4,905,082 | 2/1990 | Nishigaki et al. . |
| 4,945,409 | 7/1990 | Nakamura . |
| 4,951,133 | 8/1990 | Onoda . |
| 4,988,172 | 1/1991 | Kanamori et al. . |
| 4,995,398 | 2/1991 | Turnidge . |
| 5,021,657 | 6/1991 | Kettlewell et al. . |
| 5,133,605 | 7/1992 | Nakamura . |
| 5,147,354 | 9/1992 | Botacoff et al. . |
| 5,177,605 | 1/1993 | Takahashi et al. . |
| 5,444,250 | 8/1995 | Hanke . |
| 5,445,157 | 8/1995 | Adachi et al. . |

FOREIGN PATENT DOCUMENTS

| | | |
|---|---|---|
| 62-174713 | 7/1987 | Japan . |
| 62-174715 | 7/1987 | Japan . |
| 62-174716 | 7/1987 | Japan . |

*Primary Examiner*—John P. Leubecker
*Attorney, Agent, or Firm*—Francis J. Caufield

[57] ABSTRACT

Endodiagnostic apparatus and methods by which infrared emissions of 2 micrometers and above may be visualized in the form of encoded images to permit differential analysis. The endoscopic apparatus comprises a refractive objective lens for forming a real image of interior structure of interest, a relay system consisting solely of refractive elements for transferring the real image to an intermediate plane conjugate to the objective image plane, a refracting coupling lens for forming a final image of the intermediate image in a detector plane in which an IR detector sensitive in the range of 2 micrometers and greater may be placed near the proximal end of the apparatus, and a warm stop for ameliorating the effects of stray IR radiation in the system.

28 Claims, 11 Drawing Sheets

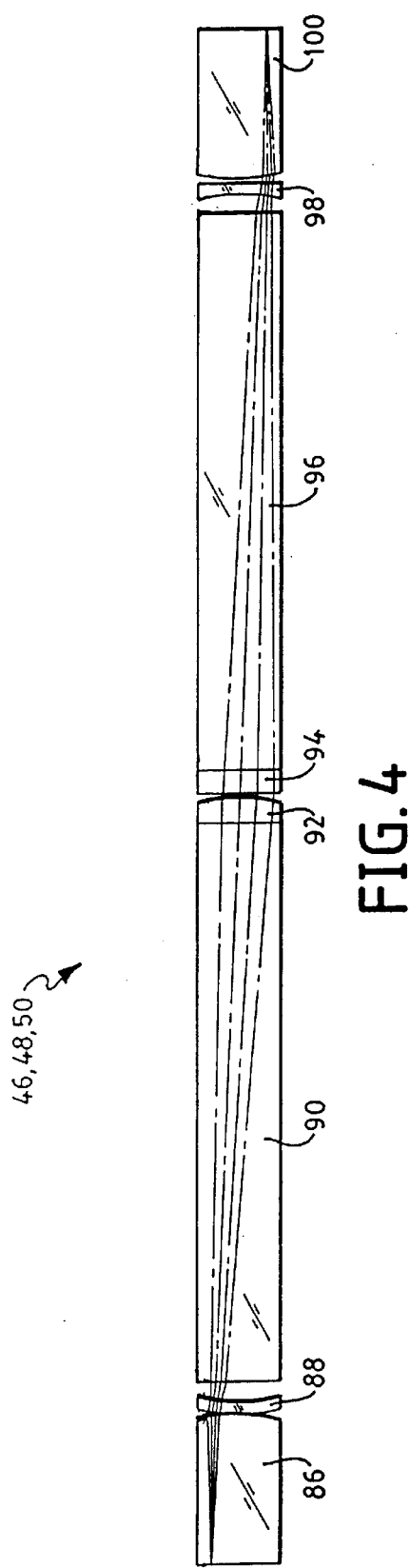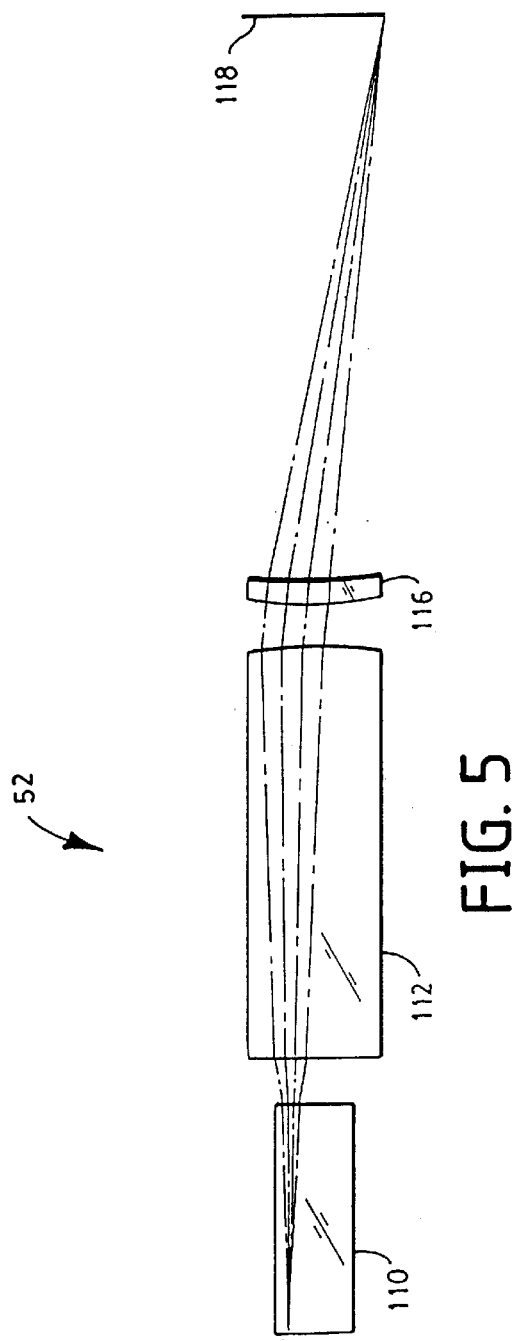

ENDOSCOPE FOR IMAGING INFRARED EMISSIONS WITHIN THE RANGE OF 2 TO 14 MICRONS

CROSS-REFERENCE TO RELATED APPLICATION

This application is a continuation-in-part of U.S. patent application Ser. No. 08/421,949 filed on Apr. 14, 1995, now U.S. Pat. No. 5,711,755.

BACKGROUND OF THE INVENTION

1. Field of the Invention

This invention relates generally to the field of endoscopic surgery and more particularly to diagnostic systems employing novel endoscopic apparatus and methods operating at and beyond the two (2) micron region of the spectrum.

2. Description of the prior Art

Endoscopic surgery (ES) continues its rapid evolutionary progress as a minimal access surgical technique that reduces patient trauma while not compromising the operating field. Operations are performed in a closed physiological environment though the use of specially designed, elongated instruments that are introduced into body cavities via relatively small cannulas (5 to 10 mm or so) and manipulated with visual guidance provided with either direct optical systems or, more recently, video systems. Compared with open surgical procedures, one major advantage of ES flows from the reduction in the severity of parietal wounds even though several cannula are usually used to gain access to the surgical sight. And, there are other advantages including a lessening of postoperative catabolic response, reduction in interior cooling and desiccation due to evaporation, fewer retraction related injuries, fewer adhesions and infections, and shorter hospital stays, along with associated costs.

ES approaches have commonly been used for laparoscopic surgery and are more frequently being adapted to other procedures such as endoluminal, perivisceral, intra-articular, thoracic, and combinations of these.

However, if the benefits of ES are to be more fully realized, diagnostic procedures are needed that will permit rapid in situ evaluation of pathology while the surgical procedures are in progress. Presently, this is not possible without significant time delays and the use of relatively complicated x-ray techniques requiring the injection of contrast dyes.

The negative impact caused by the lack of rapid least-invasive diagnostic procedures can be illustrated by considering one common ES procedure, the laparoscopic cholecystectomy for removal of the gall bladder. As is known, the cystic duct connects the gall bladder to the common bile duct which, in turn, leads to the duodenum. During a laparoscopic cholecystectomy, a diseased gall bladder is excised and removed from the body. In 3–5% of patients with diseased gall bladders, stones are not only present in the gall bladder but are also present in the cystic duct or in the vicinity of the sphincter connecting the cystic duct with the common bile duct. Retained stones present in the sphincter may cause post-operative discomfort to the patient and/or require further surgical intervention.

In the current art, this discomfort may be avoided by performing a cholangiogram during the cholecystectomy. To accomplish this, a fluoroscope is used to visualize any stones present. If a stone is observed from the cholangiogram, a secondary procedure is conducted in which a slit is made through the cystic duct. A flexible endoscope is then passed through this slit to observe the retained stones. A working channel within the flexible endoscope is equipped with a grasping forceps to remove any stones found. The flexible endoscope is of small enough diameter (~2 mm) to allow entrance into the 6 mm diameter cystic duct.

This secondary procedure has the disadvantage that it is very time-consuming and expensive because the cholecystectomy must be interrupted to bring in the fluoroscope and technician. Also, it is not preferred to expose the operating room personnel to the necessary radiation to conduct the fluoroscopy. In fact, in some 80% of the currently administered laparoscopic cholecystectomies, the cholangiogram is omitted, and the patient is at risk of having retained stones in the cystic duct.

Clearly, this and similar procedures require an alternate diagnostic tool for visualizing stones or other abnormalities while ES procedures are being conducted, and it is a primary object to this invention to provide endoscopic apparatus and methods by which such diagnoses may be conducted.

While infrared radiation has been used in the medical field for thermotreatment and other purposes, it appears to have never been used for purposes of diagnosis as advocated hereinafter. Examples of its use from the patent literature are the following:

U.S. Pat. No. 4,122,853 (Smith) discussed a means for treatment using an infrared laser beam. There is no discussion of means for viewing an IR-emitting object;

U.S. Pat. No. 4,945,409 (Nakamura) and U.S. Pat. No. 4,951,133 (Onoda) discuss miniature cameras which can be used as an endoscope in the UV, Visible, and IR. A filter from a light source rotates to choose the proper wavelength region. The IR region is confined to near IR less than one (1) micron, and there is no discussion regarding self-emission of the body in the mid-IR. Similarly, the Japanese patents are confined to near-IR wavelengths less than 1.2 microns and only to objects that are illuminated by an external source;

U.S. Pat. No. 4,418,689 (Kanazawa) describes an endoscope used with a laser. There is no discussion of an endoscope used in the infrared;

U.S. Pat. No. 4,786813 (Svanberg et.al.) describes a system for detecting fluorescence of an object. The device is limited to wavelengths less than 0.7 microns and only emissions stimulated by external excitation;

U.S. Pat. No. 4,872,458 (Kanehira et.al) describes a thermotherapy device inserted through a conventional visible light flexible or rigid endoscope. In this patent, a heat source generating far-infrared radiation is used for treatment. There is no attempt at visualizing the infrared energy through the endoscope; and U.S. Pat. No. 5,147,354 (Boutacoff et.al.) describes a fiber optic Ho:Yag laser delivery system that can be inserted through an operating channel of a conventional endoscope. Again, there is no attempt to visualize infrared energy.

Consequently, in addition to the primary purpose of the invention, it is an important purpose to provide an endoscope for visualizing interior body structures by providing visible encoded images formed from their infrared missions.

It is another object of the invention to provide endoscopic systems by which encoded images from infrared emissions from interior body structures can be observed along with images formed from visible light over the same region of interest so that diagnoses may be made via the infrared images and endosurgical procedures performed via the visible images.

It is yet another object of the present invention to provide endoscopic systems in which encoded infrared images and visible light images can be aligned in optical registration for endodiagnostic and endosurgical procedures.

It is still another object of the present invention to provide a means for the use of infrared endodiagnostic procedures for the study of the relationships among infrared images, tissue, and interior body structures to provide a basis for distinguishing normal form abnormal.

It is another object of the present invention to provide an endodiagnostic procedure for detecting the presence of residual stones during and endocholecystectomy.

It is yet another object of the present invention to provide an IR endoscope system of high spatial and temperature resolution with optimal signal throughput.

It is another object of this invention to provide a rigid IR endoscope for industrial applications.

Other objects of the invention will be apparent and will appear hereinafter in the following detailed description when read in connection with the drawings.

SUMMARY OF THE INVENTION

Endodiagnostic apparatus, systems, and methods are described by which infrared emissions from interior body structures may be visualized in the form of encoded images to permit differentiation between normal and abnormal processes. The encoded infrared images may be used along with other images from the visible spectrum to serve as an adjunct in the performance of endosurgical procedures by permitting contemporaneous endodiagnosis and are particularly efficacious for interoperative diagnosis during laproscopic surgerical procedures such as endoscopic cholecystectomy where the common bile duct requires exploration for the presence of residual stones.

An endoscopic system including an endoscope and associated camera are provided for detecting infrared emissions beyond about 2 microns and converting the detected infrared radiation into visible images in which information about the normalcy of a visualized site is encoded in the form of gray scale or colored images to permit differential diagnosis. When these infrared images are presented aside of images from radiation from the visible spectrum, pathology may be marked for later surgical procedures in the visual channel. In addition, the IR endoscope may be used for industrial applications where images are encoded for visual examination.

In both the infrared and visual channels of the endodiagnostic system, standard NTSC or PAL video signals are generated for display on video monitors and may be recorded for permanent records.

A preferred method for the visualization of residual stones in the common bile duct during endoscopic cholecystectomy involves thermal perturbation by cooling with sterile saline or Ringer's solution to cause a general depression in the temperature of the site of interest while continuously imaging with the IR endoscope. As the perturbed area proceeds toward thermal equilibrium with the surrounding body tissue temperature, any retained stones can be visualized because the rate at which they approach thermal equilibrium differs from that of the cystic duct itself.

In another embodiment, both the IR diagnostic channel and visible channel are mounted substantially coaxially in a single tube for alignment purposes, which may include compensation for parallax effects.

In addition to its usefulness in the diagnosis of residual stones, the invention is also useful for the detection and identification of abdominal fluid sacs or tumors, highly oxygenated or vascular tumors, blood vessels, and cartilage necrosis in body joints.

DESCRIPTION OF THE DRAWINGS

The structure and operation of the invention, together with other objects and advantages thereof, may best be understood by reading the detailed description in connection with the drawings in which unique reference numerals have been used throughout for each part and wherein:

FIG. 4 is an enlarged, side-elevational view of one of the relay systems comprising the infrared endoscope of FIG. 2;

FIG. 5 is an enlarged, side-elevational view of the coupler lens and infrared camera of the infrared endoscope of FIG. 2;

DETAILED DESCRIPTION

The present invention relates to endodiagnostic apparatus and methods by which infrared emissions from interior body structures may be visualized in the form of encoded images to permit differentiation between normal and abnormal processes. The encoded infrared images may be used along with other images from the visible spectrum to serve as an adjunct in the performance of endosurgical procedures by permitting contemporaneous endodiagnosis and are particularly efficacious for interoperative diagnosis during laproscopic surgerical procedures such as endoscopic cholecystectomy, where the common bile duct requires exploration for the presence of residual stones. The various embodiments of the invention are based on the recognition that significant signal levels may be derived from emissions from interior body structures in the spectral region in the range including 2 to 14 microns, and that these emissions may be selectively altered using thermal relaxation techniques to enhance the thermal contrast between normal and abnormal processes.

Figure 1:
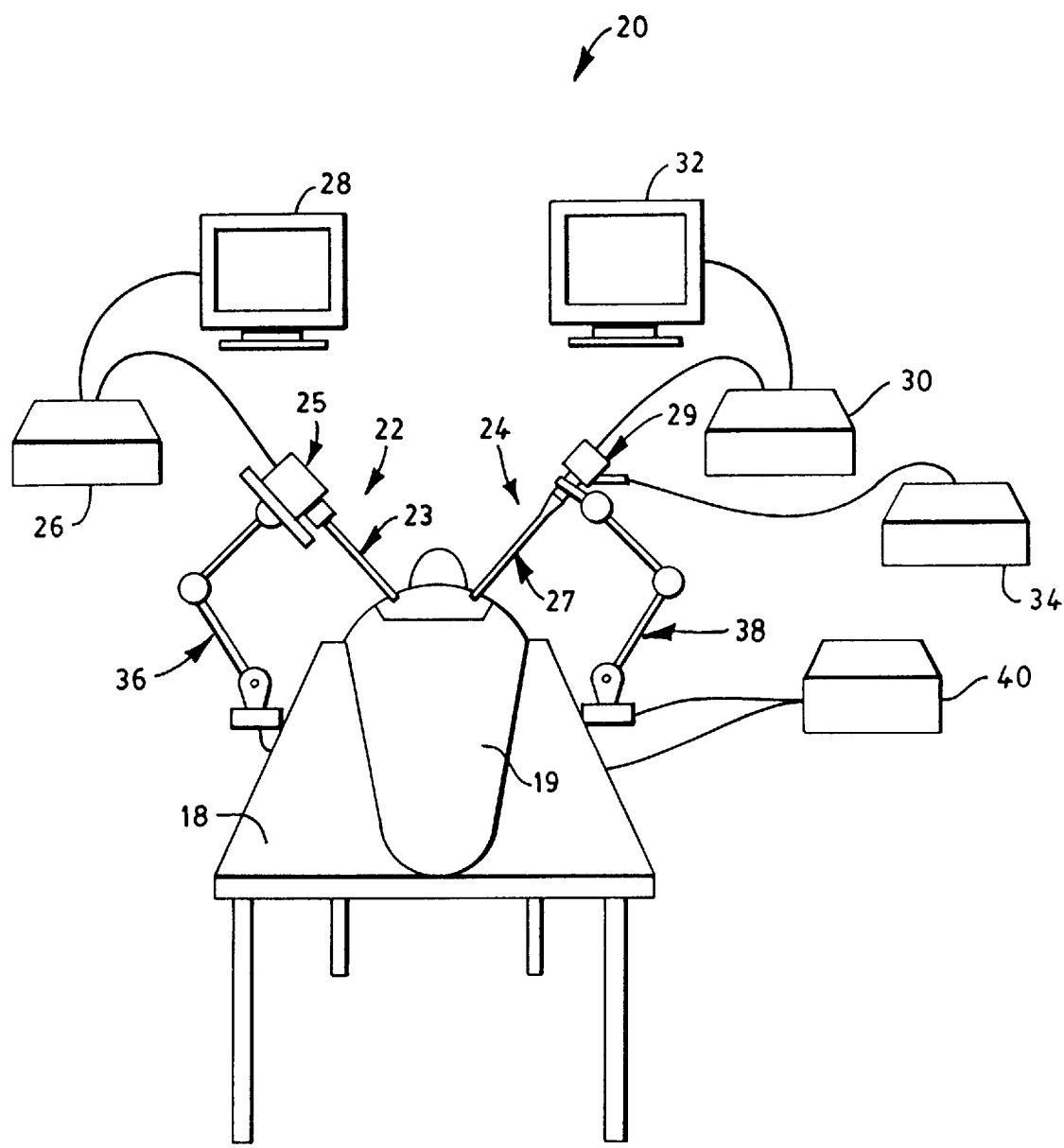
FIG. 1 is a diagrammatic perspective of an inventive diagnostic imaging system of the invention showing infrared and visible radiation endoscopic apparatus for providing encoded images from infrared emissions next to corresponding visible images of substantially the same field of interest.

One preferred embodiment of the invention, designated generally as the system 20, is shown in use FIG. 1 for performing abdominal diagnostic and/or surgical procedures on a patient 19 atop of an operating table 18. System 20 comprises an infrared (IR) endoscopic imager 22 and a visible endoscopic imager 24. IR imager 22 comprises an IR endoscope 23 and an IR video camera 25, and visible imager 24 comprises a visible endoscope 27 and a visible video camera 29.

IR video camera 25 is connected to a video controller 26 for generating standard NTSC or PAL video signals, and the video controller transmits such standard video signals to a video monitor 28 for displaying images carried on the standard video signals.

Visible video camera 29, which may comprise a CCD or vidicon detector or the like, generates a video signal, also in standard video formats, to a visible signal controller 30 which, in turn, transmits it to a video monitor 32 to display images carried via visible video signal. The video signal processing components of the invention may be of well-known conventional design.

Illumination for the visible endoscope 27 is provided by way of a visible light source and controller 34. Preferably, visible light is conducted via fiber optic cables in a manner to be more fully described hereinafter.

IR imager 22 and visible imager 24 are each carried on well-known articulable, pneumatically based and controlled robotic arms 36 and 38, respectively, and both are connected to a pneumatic source and controller 40 to permit the user to position and support the endoscopes as required. Robotic arms 36 and 38 are of the type marketed by Leonard Medical Inc., Huntingdon, Pa. under the trademark "The First Assistant™". Arms 36 and 38 are each provided with three articulating joints that are easily manipulated to permit each endoscopic imager to be moved and locked into place once the desired perspective is achieved or once the imaged fields of interest have been visually aligned in optically registered relationship. For this purpose, arms 36 and 38, are releasably clamped to table 18, and may be moved as needed for the particular imaging task at hand.

In this connection, video monitors 28 and 32 may also be mounted on articulated arms (not shown) of the type that are fastened to a wall so that the monitors may be conveniently moved for optimal viewing conditions. Also, it will be understood that each monitor may display both IR and visible images by way of well-known techniques for splitting screens.

Figure 2:
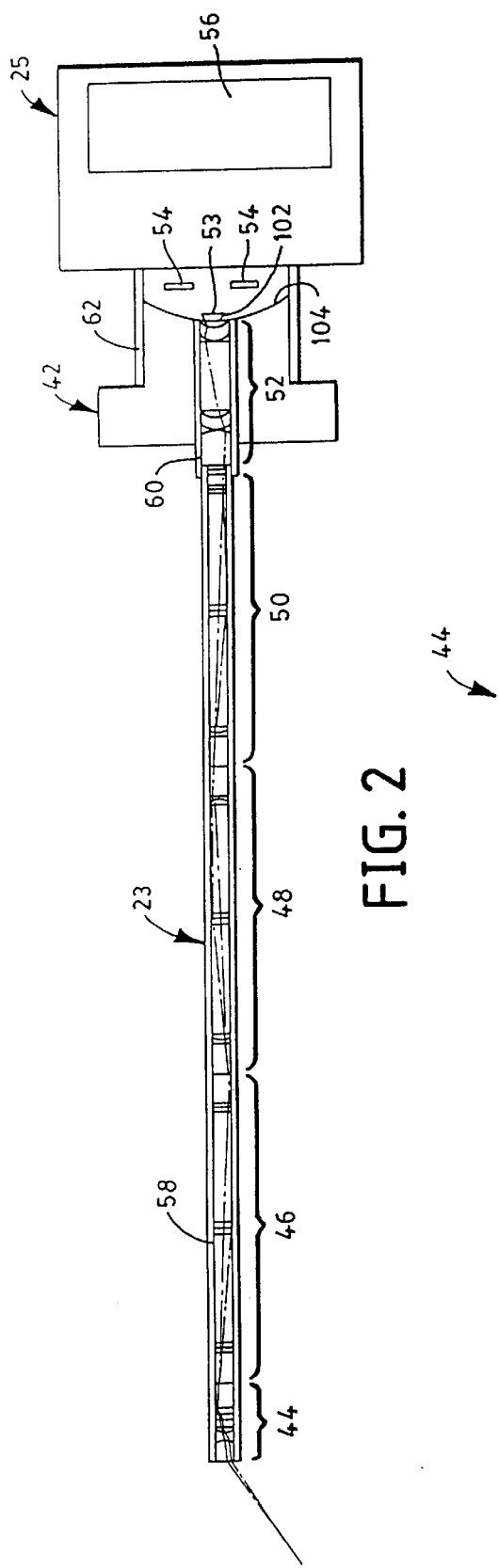
FIG. 2 is a side-elevational view of the infrared endoscope of FIG. 1 with parts shown diagrammatically.

Reference in now made to FIG. 2, which shows various components comprising IR imager 22. As can be seen there, the IR endoscope 23 comprises and objective lens 44 for collecting radiation emitted from an object of interest and forming a real image of it, three identical relay sections, 46, 48, and 50, for transferring the real image to an intermediate image plane located near the endoscope's proximal end, and a coupler lens 52 for forming an image of the intermediate image on an IR detector 53.

IR video camera 25, which includes IR detector 53, is mechanically linked and optically registered with IR endoscope 23 via an adapter 42 that also serves as a warm stop as a consequence of having integrated features for that purpose as will subsequently be explained.

Camera 25 also includes a cold stop 54 for excluding unwanted stray thermal radiation that may otherwise degrade the quality of the IR image by lowering the signal-to-noise ratio of the system.

In this embodiment, all of the elements of the optical train are refractive elements made of Germanium. The elements of objective 44 and relay sections, 46, 48, and 50, are mounted in a well-known manner, in an elongated tube 58 of appropriate length, and the elements comprising the coupler lens are mounted, again in a well-known manner in a sleeve 60 that fits into an appropriately through hole bored in adapter 42. Tube 58 is affixed to sleeve 60, and adapter 42 slides into and is fastened in place in another sleeve 62 that extends forwardly of camera 25 and is adapted to receive adapter 42 and establish its position with respect to IR detector 53 and cold stop 54.

The IR endoscope has an overall track length of 461.73 mm, its semi-field angle is 34°, its working f/# is 5.72, and the diameter of tube 58 is 10 mm so that IR endoscope 23 will fit in standard cannula openings.

Figure 3:
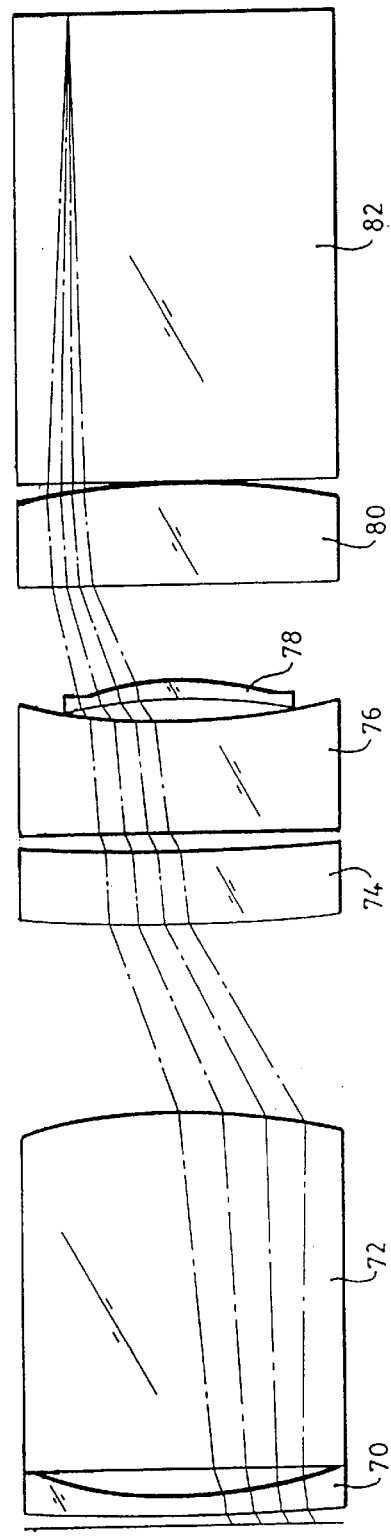
FIG. 3 is an enlarged, side-elevational view of the objective system of the infrared endoscope of FIG. 2.

As best seen in FIG. 3, objective 44 comprises seven elements, a negative meniscus 70, a thick positive double convex element 72, a positive element 74, a negative element 76, a positive meniscus 78, a positive element 80, and a slightly positive rod lens 82. The surfaces themselves are 3 through 16, respectively, in following Table I.

Reference is now made to FIG. 4, which shows a typical relay section of the invention. All of the elements of each relay are identical to those shown in FIG. 4. Three relays are used to achieve the desired length, and an odd number of relays provide an upright image in the intermediate plane, although any number can be used with image orientation handled by proper compensation with camera orientation or other well-known means such as a reversal mirror.

As can be seen in FIG. 4, a typical relay section consists of a plano convex element 86, a meniscus 88, a rod 90, a plano convex element 92, a convex plano element 94, a rod 96, a meniscus 98 and a convex piano element 100. It will be appreciated that the relay sections are symmetrical about the aperture stop of IR endoscope 23, which is between elements 92 and 94 in FIG. 4. Physically, the aperture stop is provided with a real stop made of a low emissivity material, preferably of polished aluminum and preferably coated with gold, and the image of the aperture stop is the real entrance aperture 102 located in the rear curved surface 104 of adapter 42. This is located just before IR detector 53 (See FIG. 2). The aperture stop could also be any other appropriate material coated with gold.

Aperture 102 is located in this manner in adapter 42, which in part serves as a warm stop, at the conjugate of the IR endoscope aperture stop so that it will present the smallest opening for the entry of stray thermal radiation into the IR detection system of camera 25. The various surfaces of the elements of a typical relay are set forth in Table I below as 16 through 31.

Reference is now made to FIG. 5, which shows the elements of video coupling lens 52. The intermediate image plane is shown at the circled numeral 62. Lens 52 itself comprises negative element 110, positive element 112, thick negative element 114, positive element 116, and finally image 118, which is where IR detector 53 is resident. The following table lists the constructional data for the IR endoscope 23 where dimensions are in mm. In this table, surfaces 31 through 60 simply repeat the constructional data of surfaces 16 through 31 for a typical relay section as shown in FIG. 4.

TABLE I

| Surface | Radius | Thickness | Material | Diameter |
|---|---|---|---|---|
| OBJ | Infinity | 50 | | 72.02901 |
| 1 | Infinity | 0.25 | SAPPHIRE | 7 |
| 2 | Infinity | 0.2 | | 7 |
| 3 | 57.58571 | 0.3987758 | GERMANIUM | 7 |
| 4 | 9.425214 | 0.5789028 | | 7 |
| 5 | 88.87686 | 7.627548 | GERMANIUM | 7 |
| 6 | −15.36183 | 3.957111 | | 7 |
| 7 | 38.17246 | 1.559314 | GERMANIUM | 7 |
| 8 | 47.898 | 0.3581245 | | 7 |
| 9 | 146.2148 | 2.402521 | GERMANIUM | 7 |
| 10 | 15.72048 | 0.4595021 | | 7 |
| 11 | −13.73784 | 0.3845466 | GERMANIUM | 7 |
| 12 | −6.854572 | 2.022597 | | 7 |
| 13 | 855.4531 | 2.067545 | GERMANIUM | 7 |
| 14 | −21.05445 | 0.07877675 | | 7 |
| 15 | 6793.881 | 10.0609 | GERMANIUM | 7 |
| 16 | Infinity | 12.2791 | GERMANIUM | 7 |
| 17 | −21.67682 | 0.2 | | 7 |
| 18 | 55.27044 | 1.082979 | GERMANIUM | 7 |
| 19 | 21.05387 | 1.347465 | | 7 |
| 20 | Infinity | 45 | GERMANIUM | 7 |
| 21 | Infinity | 0 | | 7 |
| 22 | Infinity | 2 | GERMANIUM | 7 |
| 23 | | −50.7869 | 0.2 | 7 |
| 24 | 50.7869 | 2 | GERMANIUM | 7 |
| 25 | Infinity | 0 | | 7 |
| 26 | Infinity | 45 | GERMANIUM | 7 |
| 27 | Infinity | 1.347465 | | 7 |
| 28 | −21.05387 | 1.082979 | GERMANIUM | 7 |
| 29 | −55.27044 | 0.2 | | 7 |
| 30 | 21.67682 | 12.2791 | GERMANIUM | 7 |
| 31 | Infinity | 12.2791 | GERMANIUM | 7 |
| 32 | −21.67682 | 0.2 | | 7 |
| 33 | 55.27044 | 1.082979 | GERMANIUM | 7 |
| 34 | 21.05387 | 1.347465 | | 7 |
| 35 | Infinity | 45 | GERMANIUM | 7 |
| 36 | Infinity | 0 | | 7 |
| 37 | Infinity | 2 | GERMANIUM | 7 |
| 38 | −50.7869 | 0.2 | | 7 |
| 39 | 50.7869 | 2 | GERMANIUM | 7 |
| 40 | Infinity | 0 | | 7 |
| 41 | Infinity | 45 | GERMANIUM | 7 |
| 42 | Infinity | 1.347465 | | 7 |
| 43 | −21.05387 | 1.082979 | GERMANIUM | 7 |
| 44 | −55.27044 | 0.2 | | 7 |
| 45 | 21.67682 | 12.2791 | GERMANIUM | 7 |
| 46 | Infinity | 12.2791 | GERMANIUM | 7 |
| 47 | −21.67682 | 0.2 | | 7 |
| 48 | 55.27044 | 1.082979 | GERMANIUM | 7 |
| 49 | 21.05387 | 1.347465 | | 7 |
| 50 | Infinity | 45 | GERMANIUM | 7 |
| 51 | Infinity | 0 | | 7 |
| 52 | Infinity | 2 | GERMANIUM | 7 |
| 53 | −50.7869 | 0.2 | | 7 |
| 54 | 50.7869 | 2 | GERMANIUM | 7 |
| 55 | Infinity | 0 | | 7 |
| 56 | Infinity | 45 | GERMANIUM | 7 |
| 57 | Infinity | 1.347465 | | 7 |
| 58 | −21.05387 | 1.082979 | GERMANIUM | 7 |
| 59 | −55.27044 | 0.2 | | 7 |
| 60 | 21.67682 | 5 | GERMANIUM | 7 |
| 61 | 53.0202 | 7.190098 | GERMANIUM | 7 |
| 62 | −1181.617 | 20 | GERMANIUM | 7 |
| 63 | 100 | 4 | | 7 |
| 64 | 220.3955 | 35.78447 | GERMANIUM | 12 |
| 65 | −65.86031 | 4 | | 12 |
| 66 | 39.62417 | 2 | GERMANIUM | 12 |
| 67 | 59.62065 | 50 | | 12 |
| 68 | Infinity | 0 | | 12.84649 |

Figure 6:
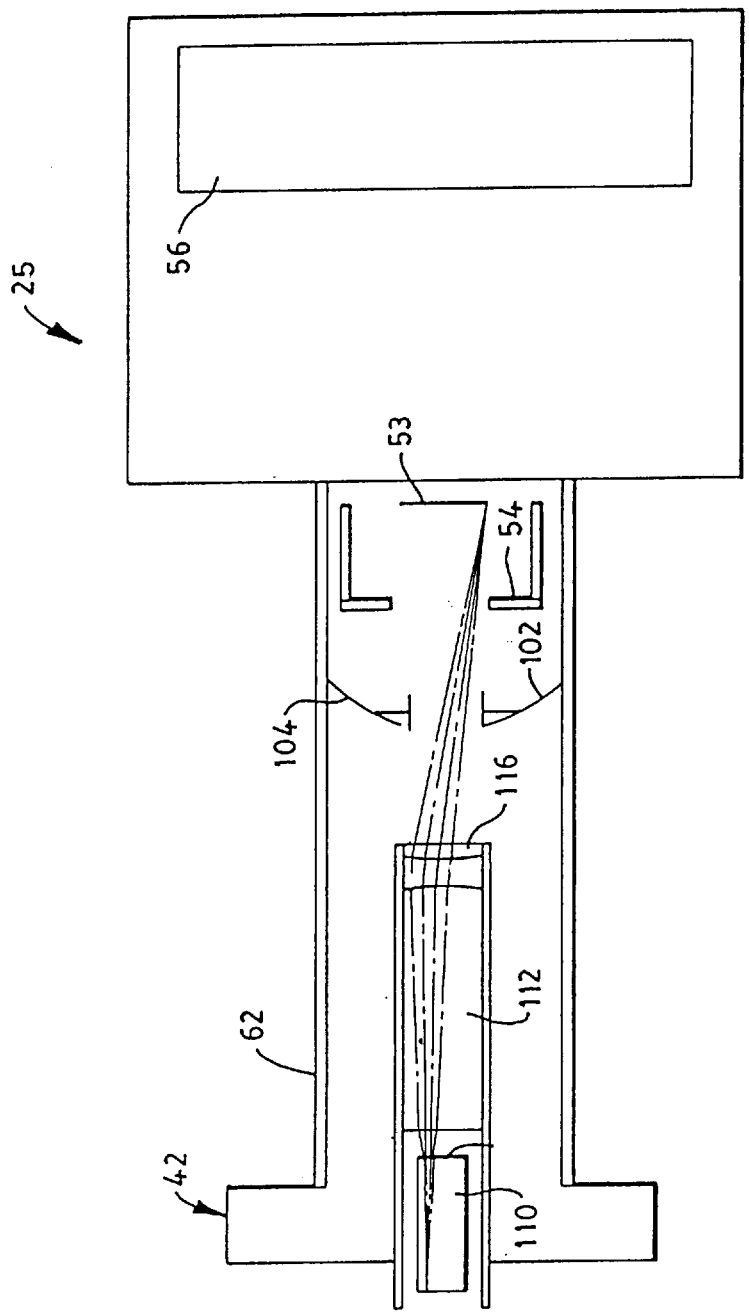
FIG. 6 is an enlarged, side-elevational view of the coupler lens of FIG. 5 shown in combination with the infrared camera of the inventive endoscopic system.

Reference is now made to FIG. 6 which shows in greater detail adapter 42 with its integral warm stop features along with detector 53 and IR video camera 25. As mentioned previously, real (physical) aperture 102 is physically positioned at the image of the aperture stop of IR endoscope 23 and as such, operates to limit the amount of stray or unwanted thermal radiation that can enter the detection system of camera 25. To further deal with the elimination of stray thermal radiation, camera 25 is provided with cold stop 54 for rejecting stray thermal radiation that might enter the detection system and cause signal degradation. Therefore, the rear surface of adapter 42 is shaped to reflect detector 53 back onto itself so that any stray radiation bouncing around in the detector cavity that finds its way into the field of detector 53, as defined in conjunction with aperture 102, is either directly absorbed by cold stop 54 or absorbed by it after one or more reflections as an image back onto cold stop 54. Preferably, detector 53 is placed in a plane that intersects the optical axis at the center of curvature of surface 104.

If a warm stop is not to be used, the field of view and f/# of the camera should be exactly matched with that of the IR endoscope within tolerances, so that only wanted radiation is collected by the camera, and any stray radiation is directly absorbed by the camera cold stop. Here, the cold stop would be at the aperture stop.

It is to be noted that the above constructional data has been optimized for image quality at 5 microns but, because of the low chromatic dispersion and flat index of refraction profile for Germanium, the image quality over the region from 2 to 14 microns will likewise be acceptable so that the inventive IR endoscope is useable over this extended range.

IR video camera 56 is to be as light weight as possible, and for this purpose is provided with only a preamplifier 56 with most of the signal amplification and control taking place in the distantly located controller 26.

One IR video camera and controller which has been found acceptable is marketed by Amber Corporation, A Raytheon Company, of Goleta, Calif., under the trade name RADIANCE 1. This camera has an Indium Antimonide (InSb) detector with 256×256 picture elements and a spectral bandpass of from 3 to 5 microns.

Figure 7:
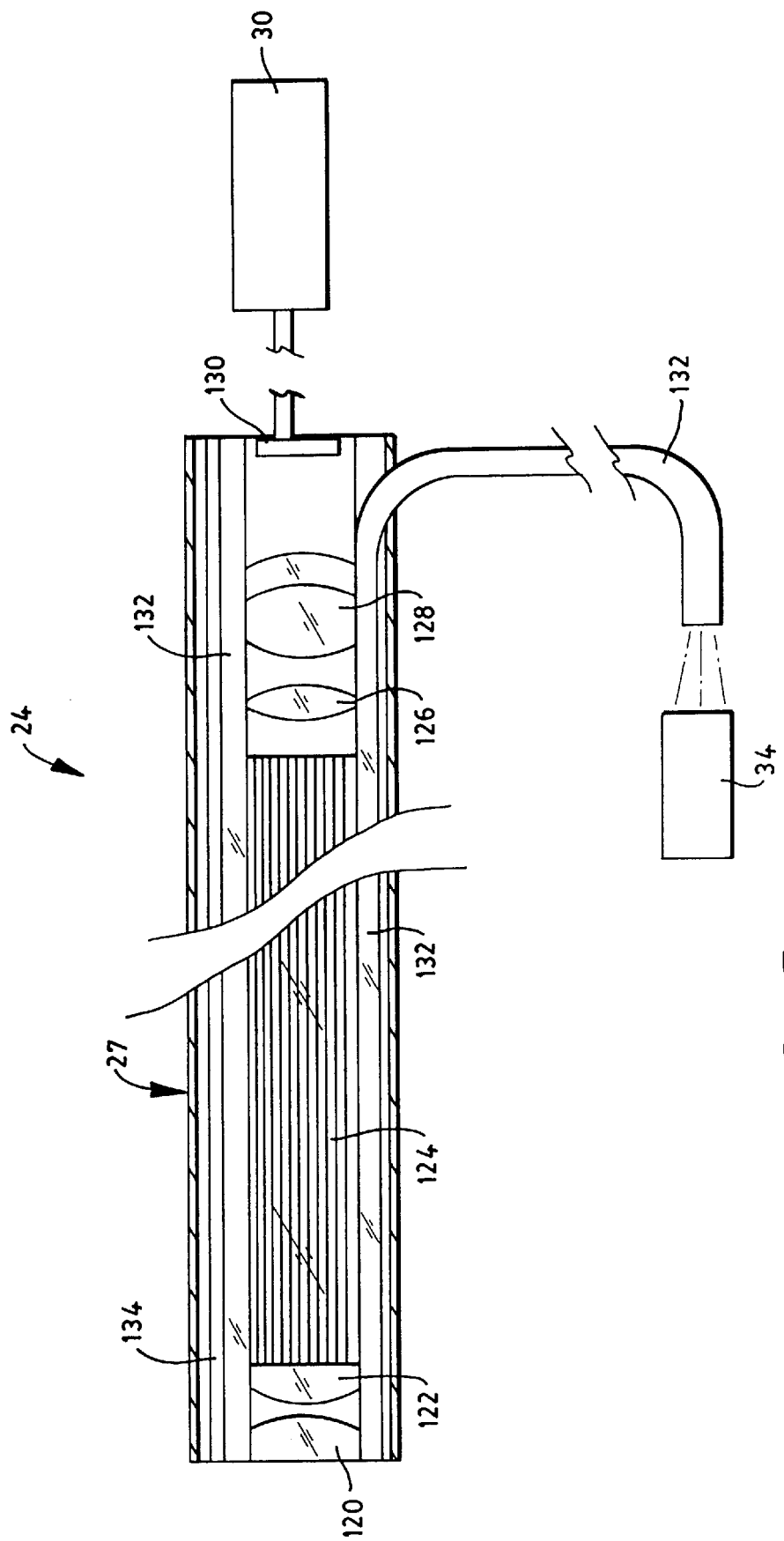
FIG. 7 is an enlarged, diagrammatic, side-elevational view of the visible light endoscope of the system of FIG. 1.

Reference is now made to FIG. 7 which shows the visible endoscope 24. It is seen to comprise an objective which includes two symmetrically arranged piano convex elements, 120 and 122, respectively, which form an image onto or near the end of a coherent fiber optic bundle 124 which transfers the image to the proximal end of the endoscope where it is imaged by a video coupler lens onto a CCD 130. The video coupler lens comprises a singlet 126 followed by a doublet 128. All of the elements of visible endoscope 24 are of well-known design.

Illumination is by way of a fiber bundle 132 which accepts visible light from source and controller 34 and directs it along side the viewing channel toward the distal end for rendering internal body structures visible.

Along side the illumination system, or coaxial with it, is an irrigation channel 134 that may be used to conduct cooling solutions to the internal site being observed for purposes of providing enhanced thermal contrast to those regions in a manner to be described.

Figure 8:
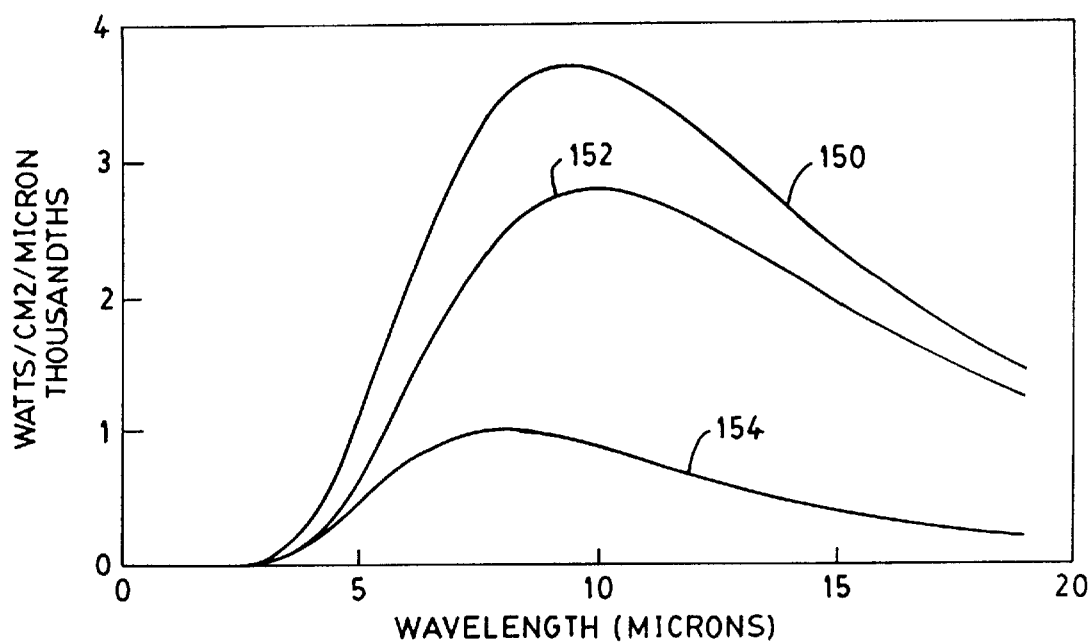
FIG. 8 is a graph showing the infrared radiant emissions from bodies at 98.6° F. and 68° F., along with the difference in IR emissions between them.

The endoscopic system of the invention, thus structured, permits the visualization of otherwise invisible features of internal body structures through the expediency of detecting radiation they emit in the infrared region of the spectrum within the range between 2 and 14 microns. If one looks at FIG. 8, it can be seen that the human body considered as a black body at 98.6° F. (curve 150) has a radiation curve which emits from about 2 to 20 microns with most emissions occurring between about 4 to 15 microns. Consequently, this range of emitted energy has been found sufficient for imaging purposes even at the scale of endoscopes. Moreover, it has been observed that even different body structures at the same temperature will image differently because of differences in their thermal emissivities. Consequently, the IR imager of the present invention is capable of mapping the detected IR emissions as images encoded as differences in either gray scale (monochromatic) or colors (from preselected gamuts) for purposes of providing differential diagnoses which are indicative of normal from abnormal. In addition, it has been found that the addition of cooling solutions to a site of interest will suppress the temperature of that site at least temporarily so that its emissions may look somewhat like curve 152 in FIG. 8, which is for a black body at 68° F., or room temperature. As a site temporarily cooled to room temperature gradually warms up, i.e., approaches thermal equilibrium with its surroundings, here body temperature, it will do so but at different rates corresponding to the thermal properties of the different structures of which it is composed. Therefore, different amounts of thermal energy will be emitted and can be detected to form images. This phenomenon can be exploited since there will typically be a differential heat emission given off by a region that has been temporarily cooled as evidenced by curve 154 in FIG. 8, which shows the difference in thermal energy between curves 150 and 152.

In one particularly important circumstance, the foregoing observations may be beneficially practiced to solve a significant problem that occurs frequently in connection with the removal of gall bladders. As is well-known, the cystic duct connects the gall bladder to the common bile duct which in turn leads to the duodenum. During a laparoscopic cholecystectomy, a diseased gall bladder is excised and removed from the body. In 3–5% of patients with diseased gall bladders, stones are not only present in the gall bladder but are also present in the cystic duct, or in the vicinity of the sphincter connecting the cystic duct with the common bile duct. Retained stones present in this sphincter may cause post-operative discomfort to the patient or require follow-on surgical intervention. In the current art, to avoid this discomfort, a cholangiogram is conducted during the cholecystectomy. The cholangiogram involves the use of a fluoroscope to visualize any stones present. If a stone is observed from the cholangiogram, a secondary procedure is conducted in which a slit is made through the cystic duct. A flexible endoscope is then passed through this slit to observe the retained stones. A working channel within the flexible endoscope is equipped with a grasping forceps to remove any stones found. The flexible endoscope is of small enough diameter (~2 mm) to allow entrance into the 6 mm diameter cystic duct.

This secondary procedure has the disadvantage that it is very time-consuming and expensive to interrupt the cholecystectomy to bring in the fluoroscope and technician. Also, it is not preferred to expose the operating room personnel to the radiation necessary for conducting the fluoroscopy. In fact, in some 80% of the currently administered laparoscopic cholecystectomies, the cholangiogram is omitted and the patient is at risk of having retained stones in the cystic duct and associated complications.

In the method of the present invention, diagnosing retained stones in the cystic duct is accomplished by using infrared laparoscopy. The usual visual laparoscope may be temporarily replaced by an infrared laparoscope having approximately the same diameter so that it can be positioned through the same cannula as the visual laparoscope or the IR laparoscope may have two optical channels, one to provide an image using scattered visible illumination and one to provide an image using IR self-emitted from the body. In an alternate embodiment, a single optical channel may be used to provide both visible and IR images with the two separately proximally using a beamsplitter. No operating channels are used in the preferred embodiment since it is preferable to obtain greater parallax by using an auxiliary operating channel (not shown).

The optical channel containing the visible light forming optics uses conventional lenses such as those present in commercial instruments made by many companies including Circon/ACMI, Storz, Wolf, and others. The visible light optical channel uses a conventional video sensor also available through the foregoing companies. The optical channel containing the infrared light forming optics uses transparent materials in the infrared portion of the spectrum. The IR light optical channel may use one of two types of infrared video sensor. The first type (Indium Antimonide) has relatively high resolution and is most sensitive at about 5 micrometer. A second type, HgCdTe, has relatively poor resolution but is sensitive in the 8–12 micrometer range which is near the peak black body emission curve corresponding to the human body. Also, and preferably, this method uses two separate endoscopes of the type described hereinabove.

Figure 9:
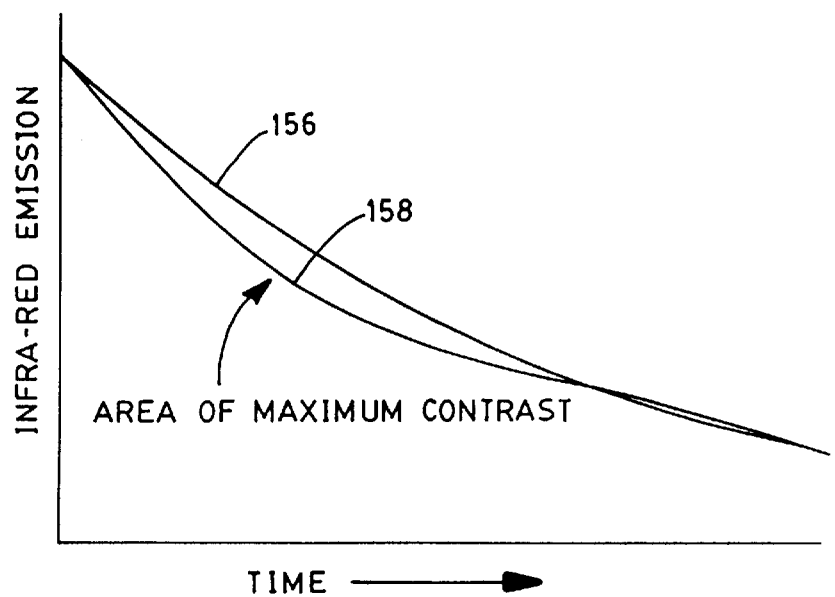
FIG. 9 is a graph illustrating the principle of a differential thermal relaxation method used in practicing one aspect of the invention.

The principal by which the IR laparoscope operates in this instance is by differential thermal relaxation. The area of interest is flushed with room-temperature sterile saline or Ringer's solution. Upon contact with the area of interest (which would include to general area of the cystic duct and sphincter to the common bile duct), an immediate cooling of the flush site will take place. It should be noted that this irrigation may also be by any commonly used sterile fluid dispenser wand made by companies such as C. R. Bard, Johnson & Johnson, and U.S. Surgical Corporation. This room temperature flush provides a temperature differential of approximately 25 degrees Fahrenheit compared to surrounding body-temperature tissue. As the area warms back to the surrounding tissue temperature, any retained stones can be visualized because their temperature warms at a different rate compared to the cystic duct itself. This is illustrated with reference to FIG. 9 where curves 156 and 158 show the different rates, respectively, at which the cystic duct and retained stones return to thermal equilibrium.

As time progresses the contrast between the retained stones and the cystic duct reaches a maximum (see again FIG. 9) and then declines as both the retained stones and cystic duct relax back to body temperature. In addition to the diagnosis of retained stones in the cystic duct, there are other endoscopic procedures that can be improved by a similar infrared technique as described above. These include: diagnosis of fluid sacs or tumors in the abdominal area and diagnosis of highly oxygenated or vascular tumors. In addition, diagnosis of cartilage necrosis in the joints of the body also appears possible.

Figure 10:
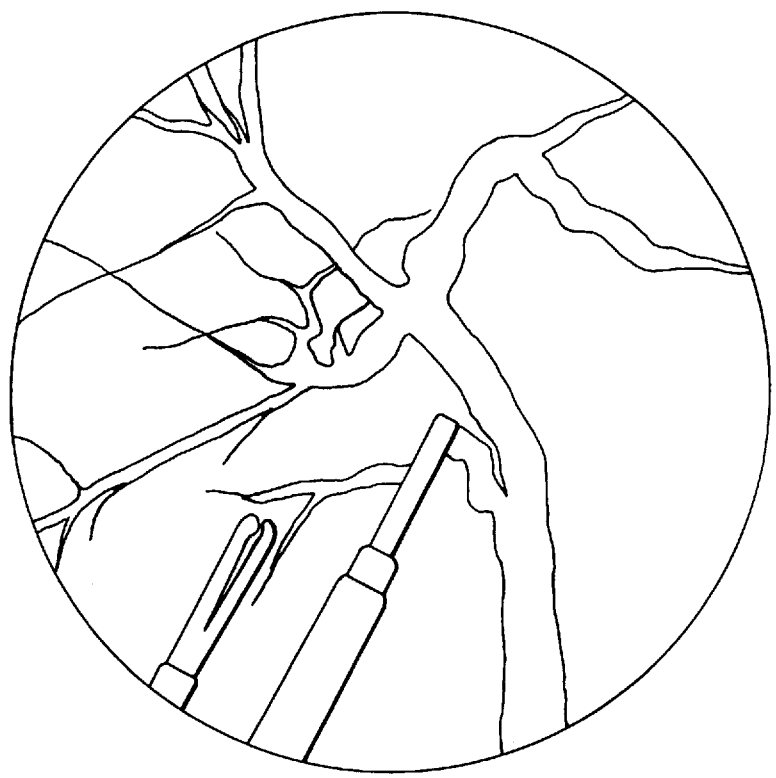
FIG. 10 is a representation of an infrared image of the sort that may be obtained utilizing the invention.

FIG. 10 illustrates how such an infrared image may appear. It shows that instruments, such as clamps may be used to identify or mark abnormal sites in the IR image which then can more easily be operated on via the visible image.

Figure 11:
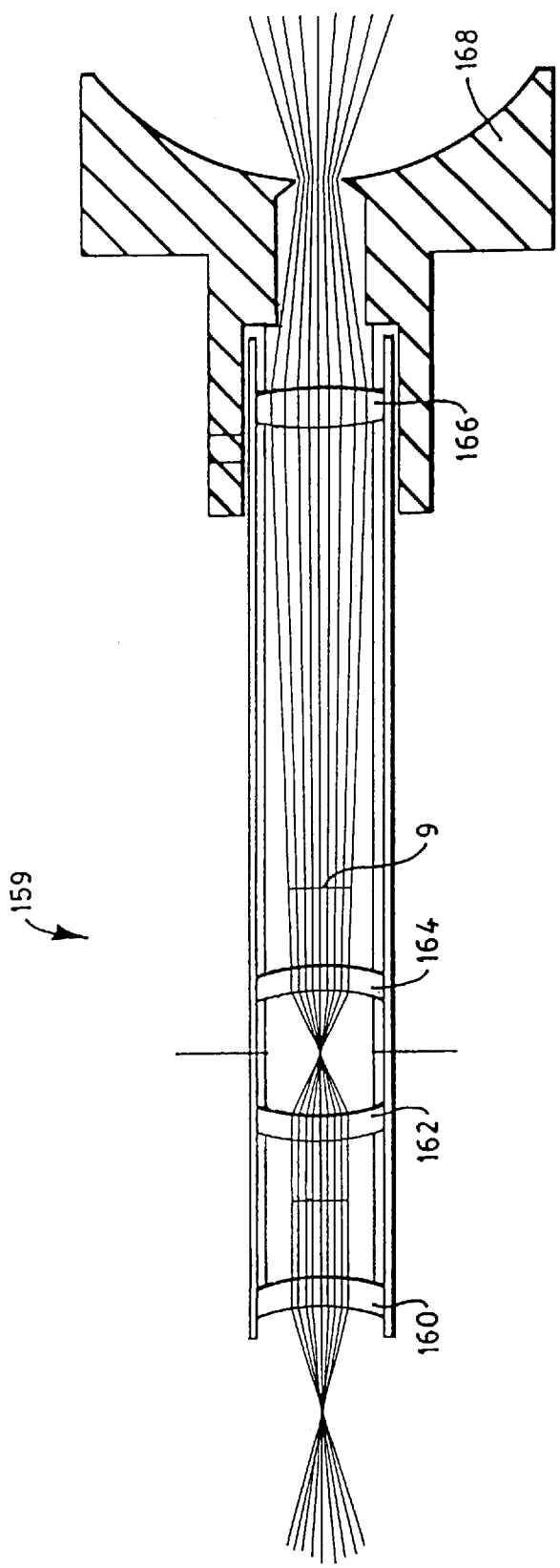
FIG. 11 is an alternate embodiment of infrared endoscope according to the invention.

An alternate version of an IR endoscope suitable for practicing the invention is shown in FIG. 11. This version which is designated generally at 159 consists of a germanium objective lens 160, a relay consisting of germanium lenses 162 and 164, a silicon video coupler lens 166, and a warm stop/adapter 168 designed similar in principle to the one described hereinabove.

The constructional data for IR endoscope 159, which includes aspheric surfaces, is given as follows where the circled numerals in FIG. 11 correspond to surfaces called out in the tabular data below:

GENERAL LENS DATA:

| | |
|---|---|
| Surfaces | 13 |
| Stop | 6 |
| System Aperture | Entrance Pupil Diameter |
| Ray aiming | On Pupil shift = 0 |
| Gaussian Factor | 0.000000 |
| Eff. Focal Len. | 6.61067 |
| Total Track | 144.16 |
| Image Space F/# | 9.72158 |
| Working F/# | 10.787 |
| Obj. Space N.A. | 0.0185359 |
| Stop Radius | −0.35032 |
| Parax. Ima. Hgt. | 5.00554 |
| Parax. Mag. | −0.404643 |
| Entr. Pup. Dia. | 0.68 |
| Entr. Pup. Pos. | −6.66032 |
| Exit Pupil Dia. | 2.24468 |
| Exit Pupil Pos. | −22.7945 |
| Maximum Field | 34 |
| Primary Wave | 4.000000 |
| Lens Units | Millimeters |
| Angular Mag. | 0.302939 |
| Coeff on r 14 | 0 |
| Coeff on r 16 | 0 |
| Surface 3 | STANDARD |
| Aperture | Circular Aperture |
| Minimum Radius | 0 |
| Maximum Radius | 3.6 |
| Surface 4 | EVENASPH |
| Coeff on r 2 | −5.8285e-005 |
| Coeff on r 4 | 2.2923e-007 |
| Coeff on r 6 | −1.5706e-009 |
| Coeff on r 8 | 0 |
| Coeff on r 10 | 0 |
| Coeff on r 12 | 0 |
| Coeff on r 14 | 0 |
| Coeff on r 16 | 0 |
| Surface 5 | STANDARD |
| Surface STO | STANDARD |
| Surface 7 | STANDARD |
| Surface 8 | EVENASPH |
| Coeff on r 2 | 5.8285e-005 |
| Coeff on r 4 | −2.2923e-007 |
| Coeff on r 6 | 1.5706e-009 |
| Coeff on r 8 | 0 |
| Coeff on r 10 | 0 |
| Coeff on r 12 | 0 |
| Coeff on r 14 | 0 |
| Coeff on r 16 | 0 |
| Surface 9 | STANDARD |
| Surface 10 | STANDARD |
| Surface 11 | STANDARD |
| Surface 12 | STANDARD |
| Aperture | Circular Aperture |
| Minimum Radius | 0 |
| Maximum Radius | 2.2 |
| Surface IMA | STANDARD |

Figure 12:
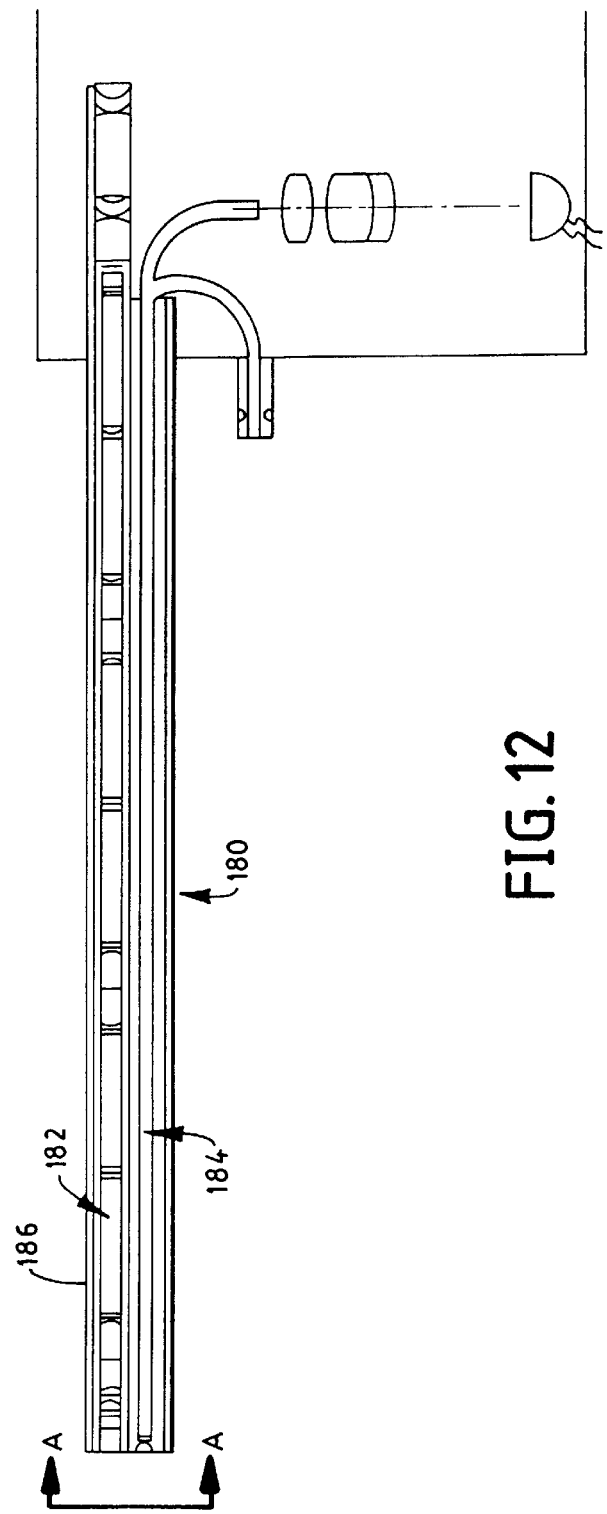
FIG. 12 is another embodiment of the invention in which the infrared and visible endoscopes have been combined for alignment purposes adjacent one another in one tube.
Figure 13:
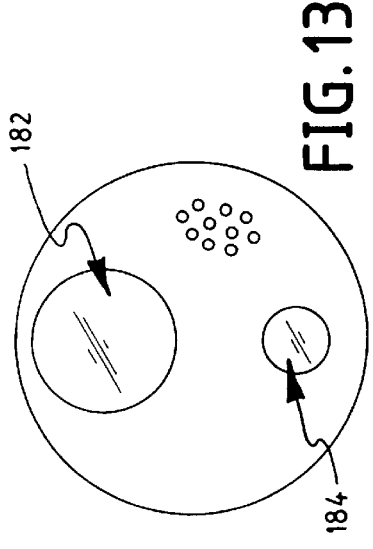
FIG. 13 is a front-elevational view of the endoscope of FIG. 12 looking along the optical axis as indicated by the line A—A.

Reference is now made to FIGS. 12 and which show an embodiment 180 of the invention in which an IR endoscope 182 and a visible endoscope 184 are resident in a common tube 186 such that they are coaxially aligned to provide overlapping views of common fields representing IR images and visible images. The overlapping views would, of course, contain common subject matter that is substantially coextensive. Here, the visible channel may be made substantially smaller in diameter than the IR channel so that the two may still be used with standard sized cannula up to about 15 mm.

Figure 14:
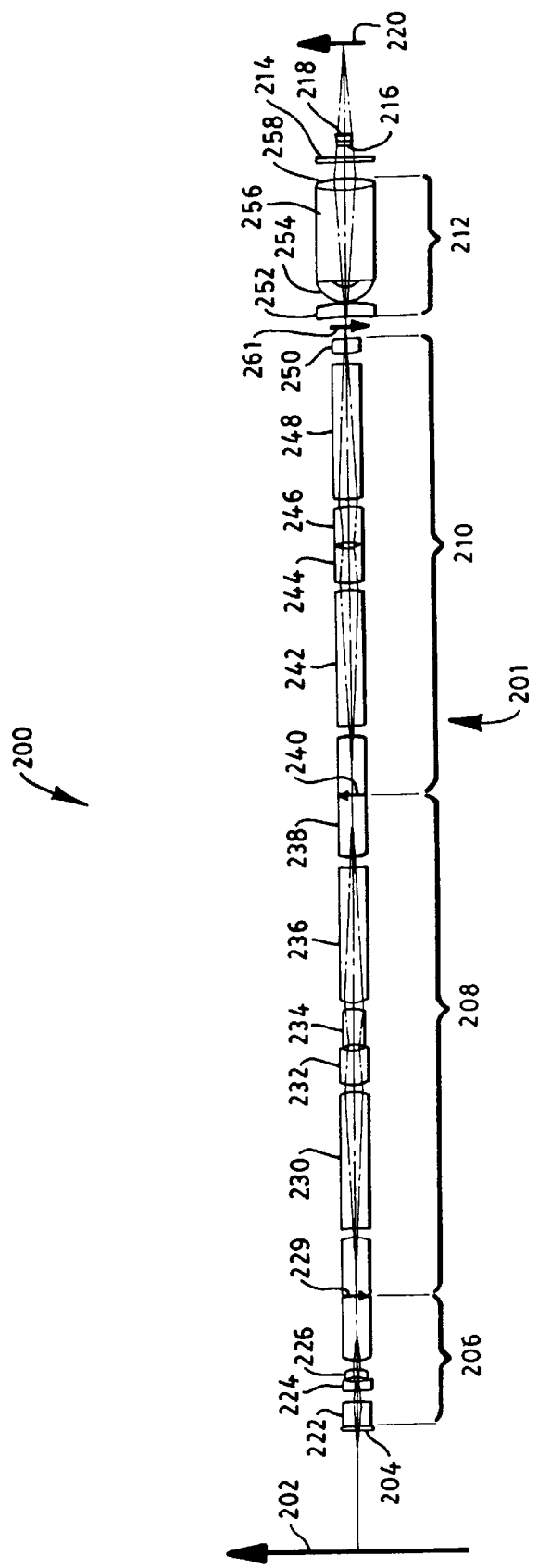
FIG. 14 is a diagrammatic side-elevational view of another preferred embodiment of an IR endoscope according to the invention.
Figure 15:
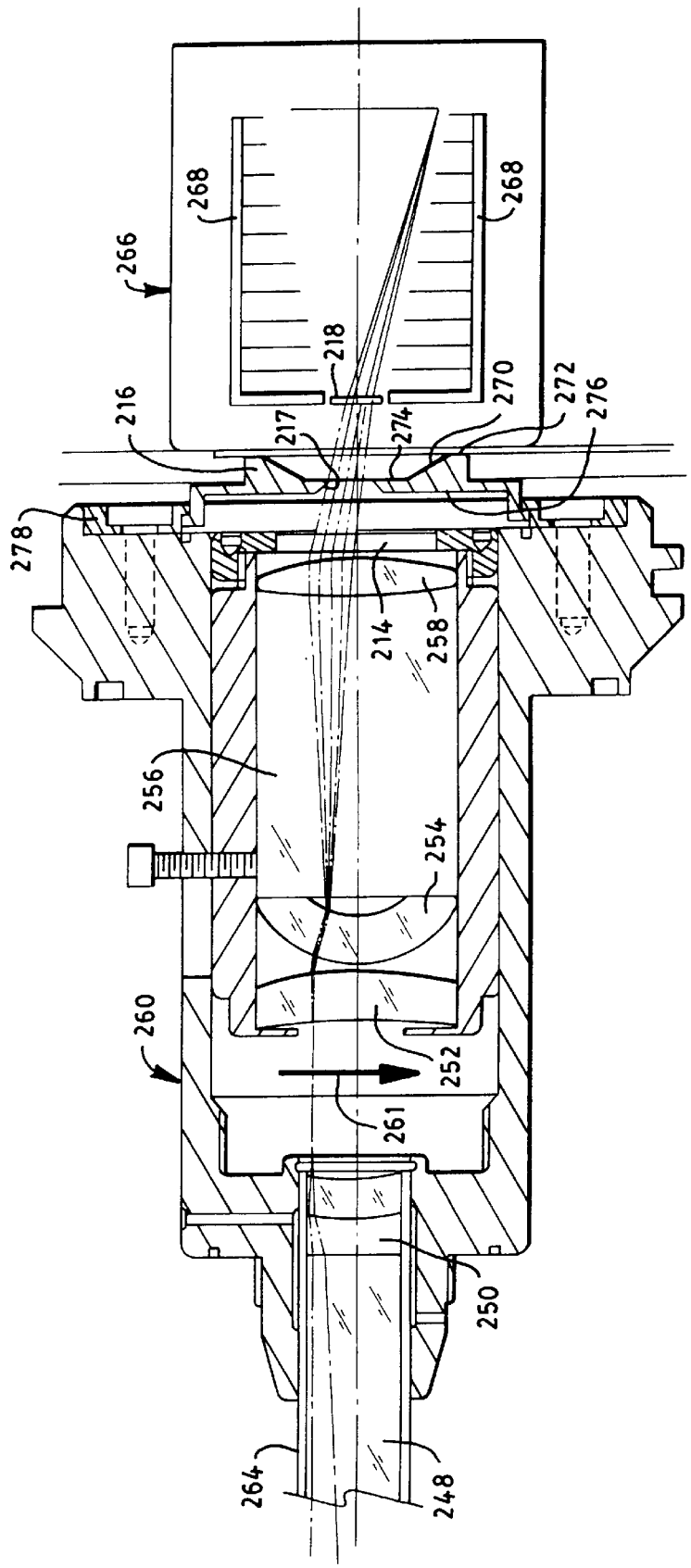
FIG. 15 is an enlarged, diagrammatic side-elevational view of a portion of the endoscope of FIG. 14 shown in combination with an adapter and an IR camera.

Another preferred embodiment of the endoscopic system of the invention is shown in FIGS. 14 and 15 where it is generally designated at 200. As before, system 200 comprises an IR endoscope 201 in combination with an infrared camera 266 which removably connects with endoscope 201 via an adapter 260. System 200 is especially suitable for medical applications because of its high spatial and temperature resolution. At a working wavelength of 4.5μ, it is able to resolve details on the order of 60μ in image space and has a temperature resolution of better than 0.1° C. provided use is made of an adequately sensitive detector such as InSb, thus making it particularly suitable for detecting small pathology features where those features exhibit small temperature differentials.

Reference in now made to FIG. 14, which shows various components comprising system 200. As can be seen there, IR endoscope 201 comprises a window 204, an and objective lens 206 for collecting radiation emitted from an object of interest and forming a real image of it, two substantially identical relay sections 208 and 210 for transferring the real image formed by objective 206 to an intermediate image plane located near the endoscope's proximal end, and a coupler or camera objective lens 212 for forming an image of the last intermediate image on an IR detector 220 located inside camera 266.

IR camera 266, which includes IR detector 220 and is a video camera as before, is mechanically linked and optically registered with IR endoscope 201 via adapter 260 which also includes a warm stop as a consequence of having integrated features for that purpose as will subsequently be explained. Adapter 260 also serves as the lens mount for coupler lens 212 and is structured to allow coupler lens 212 to be moved so that it can focus on the intermediate image relayed to it by the upstream optics.

Camera 266 also includes a cold stop 218 for excluding unwanted stray thermal radiation that may otherwise degrade the quality of the IR image. The presence of the cold stop and a novel warm stop design enhance the signal to noise ratio and reduce the presence of Narcissus effects as will be explained subsequently.

In this embodiment, most, but not all of the elements of the optical train are refractive elements made of Germanium. However, some of the elements are of AMTIR-1 that is present primarily to reduce chromatic aberrations but also contributes to the reduction of monochromatic aberrations. The elements of objective 206 and relay sections, 208 and 210, are mounted in a well-known manner, in an elongated tube 264 (a section of which is shown in FIG. 15 but otherwise not in FIG. 14) of appropriate length, and the elements comprising the coupler lens are mounted, again in a well-known manner, in a sleeve 262 that fits into an appropriately through hole bored in adapter 260. Tube 264 is affixed to a sleeve 276, and adapter 260 slides over and is fastened in place over a coupler ring 278 that extends forwardly of camera 266 and is adapted to receive adapter 260 and establish its position with respect to IR detector 220 and cold stop 218.

IR endoscope 201 has an overall track length of 375 mm, its semi-field angle is 40°, its working f/# is 5.5, and the diameter of tube 264 is 10 mm so that IR endoscope 201 will fit in standard laproscopic cannula openings.

As best seen in FIG. 14, objective 206 comprises three elements and a portion of another. More particularly, objective 206 comprises a field widening negative lens 222, a negative element 224 of AMTIR-1, a positive element 226, and the front portion of element 228. Configured in this manner, objective 206 forms an inverted image inside of element 228 where the image is free from contamination from sources such as moisture or dust. Window 204 is made of robust sapphire to protect the other elements of endoscope 201 damage, particularly their anti-reflection coatings, and serves as a seal for endoscope 201, protecting it from optically hazardous environments found in its use and cleaning.

First relay section 208 comprises the latter portion of element 228, which combines with the front surface of element 230 to provide a field lens function, and elements 230, 232, 234, 236 and the forward portion of element 238. An intermediate image is formed at 240 in element 238 and, as before, is free of the usual problems that images in air or a free surface would experience. Thus structured, the objective and relay section share a common element which performs both objective and relay functions.

Second relay section 210 comprises the rear portion of element 238, and elements 242, 244, 246, 248, and 250. Relay section 210 forms an inverted image at 261. Coupler lens 212 takes the image at 261 and forms it on detector 220. Since there are an even number of relay sections, the final image is properly oriented electronically by well-known video signal processing techniques.

While two relay sections are preferred for medical applications to achieve appropriate overall length and high throughput because of less optical path length and surfaces, odd numbers of relays may be used for other applications to achieve length requirements because the losses introduced by adding additional relay sections, as will become apparent, would be acceptable for many other applications where as high a temperature resolution were not needed. Again, image orientation can be handled by proper compensation with camera orientation.

As can be seen in FIG. 14, each relay consists of four separate elements—symmetrical pairs (e.g., 232 and 234) bracketed by rod lenses (e.g., 230 and 236), and the rod lenses each are, in turn, bracketed by a portion of another rod-like element (e.g., 228 and 238) which partially perform field lens functions. All of the relay section elements of endoscope 200 are of made of high quality germanium of low absorption (0.3 percent per cm), and the other elements of the system, where of germanium, are also of like specification.

Physically, the system aperture stop is provided as a real stop 217 formed in warm stop 216 which is made of a low emissivity material, preferably of polished aluminum and preferably coated with gold. Warm stop 216 with aperture stop 217 is located just before cold stop 218 and IR detector 220. The aperture stop could also be of any other appropriate low-emissivity material having specular surfaces coated with gold. Aperture 217 is located in this manner in adapter 260 so that it will present the smallest opening for the entry of stray thermal radiation into the IR detection system of camera 266.

Reference is now made to FIG. 15, which shows the elements of video coupling lens 212. The intermediate image plane is shown at the numeral 261. Coupler lens 212 itself comprises positive element 252, meniscus element 254, thick negative element 256, and positive element 258. The final image is coincident with detector 220 which lies in the plane of best focus for the system.

The following Table II lists the constructional data for the IR endoscope 200 where dimensions are in mm. In Table II, some of the diameters of some of the elements are reported to be smaller than others, but in practice all elements, except those of the coupler lens 212, would be of the same diameter to facilitate fabrication and assembly in tube 264. What is reported in the table are the diameters for the clear apertures. The physical diameters may be made larger for ease of assembly.

TABLE II

| Element | Surface | Radius | Thickness | Glass | Diameter |
|---|---|---|---|---|---|
|  | OBJ | Infinity | 38 |  | 69.51491 |
| 204 | 1 | Infinity | 1 | SAPPHIRE | 9.7028 |
|  | 2 | Infinity | 0.2823707 |  | 8.7 |
| 222 | 3 | −33.63722 | 7.82269 | GERMANIUM | 8.7 |
|  | 4 | −28.4607 | 3.321847 |  | 6.573973 |
| 224 | 5 | Infinity | 2.934969 | AMTIR-1 | 3.320549 |
|  | 6 | 21.22424 | 0.8502458 |  | 8.7 |
| 226 | 7 | −23.87346 | 2.440304 | GERMANIUM | 6.006383 |
|  | 8 | −10.51052 | 3.243984 |  | 7.224755 |
| 228 | 9 | 44.92244 | 35.42545 | GERMANIUM | 8.315538 |
|  | 10 | −44.92244 | 2.933372 |  | 8.500042 |
| 230 | 11 | −67.0306 | 39.93511 | GERMANIUM | 8.7 |
|  | 12 | −50.79746 | 2.44055 |  | 8.500019 |
| 232 | 13 | 23.87346 | 10.38484 | GERMANIUM | 7.226883 |
|  | 14 | 16.17904 | 1.191465 |  | 8.7 |
| 234 | 15 | −16.17904 | 10.38484 | GERMANIUM | 3.885545 |
|  | 16 | −23.87346 | 2.44055 |  | 7.101121 |
| 236 | 17 | 50.79746 | 39.93511 | GERMANIUM | 8.355493 |
|  | 18 | 67.0306 | 2.933372 |  | 7.59178 |
| 238 | 19 | 44.92244 | 35.42545 | GERMANIUM | 8.406176 |
| 240, image | 20 | −44.92244 | 2.933372 |  | 8.405971 |
| 242 | 21 | −67.0306 | 39.93511 | GERMANIUM | 7.597597 |
|  | 22 | −50.79746 | 2.44055 |  | 8.38282 |
| 244 | 23 | 23.87346 | 10.38484 | GERMANIUM | 7.128682 |
|  | 24 | 16.17904 | 1.191465 |  | 8.7 |
| 246 | 25 | −16.17904 | 10.38484 | GERMANIUM | 8.7 |
|  | 26 | −23.87346 | 2.44055 |  | 7.200055 |
| 248 | 27 | 50.79746 | 39.93511 | GERMANIUM | 8.473343 |
|  | 28 | 67.0306 | 2.933372 |  | 7.681321 |
| 250 | 29 | 44.92244 | 4.360447 | GERMANIUM | 8.500007 |
|  | 30 | 139.0929 | 3.733955 |  | 8.177104 |
| 261, image | 31 | Infinity | 2.908821 |  | 7.698674 |
| 252 | 32 | −139.0929 | 4.360447 | GERMANIUM | 16 |
|  | 33 | −44.92244 | 0.6654 |  | 18 |
| 254 | 34 | 11.20902 | 4.126468 | GERMANIUM | 18 |
|  | 35 | 7.2009 | 1.462381 |  | 8.7 |
| 256 | 36 | Infinity | 26.75623 | AMTIR-1 | 18 |
|  | 37 | 38.99154 | 0.4084151 |  | 16 |
| 258 | 38 | 76.21524 | 3 | GERMANIUM | 18 |
|  | 39 | −36.02228 | 5.451467 |  | 18 |
| 214 | 40 | Infinity | 1 | SAPPHIRE | 18 |
|  | 41 | Infinity | 4 |  | 18 |
|  | STO | Infinity | 1.016 | SILICON | 4.657658 |
| 216, warm stop | 43 | Infinity | 1.7272 |  | 5 |
| 218, cold stop | 44 | Infinity | 0.508 | SAPPHIRE | 5.312331 |
|  | 45 | Infinity | 26.162 |  | 5.409775 |
| 220, detector | IM A | Infinity | 0 |  | 13.88747 |

Reference is now made to FIG. 15 which shows in greater detail adapter 260 with its integral warm stop features along with detector 220, cold stop 218, and camera baffles 268. These elements cooperate in a novel manner to permit the camera objective elements to be smaller and hence more lightweight and inexpensive than in more traditional designs. Also, the structure and placement of warm stop 216 not only reduces the effects of stray radiation, radiation outside of the system's intended field of view determined primarily by the detector's position and size and lens focal length, but ameliorates Narcissus effects. For the foregoing purposes, warm stop 216 is provided with at least one frustro-conical surface 270 which connects to a flat surface 274. Another flat surface 272 butts against camera 26, and all of these surfaces are polished. Warm stop 216 also includes a front surface 276 that faces the distal end of endoscope 200 and is roughened and black anodized to reduce the effects of stray radiation. The surfaces of warm stop 216 facing detector 220 and baffles 268 of camera 266 have been intentionally structured as radiation control surfaces that act by reflection to direct stray Narcissus radiation onto detector 220 in a defocused manner or onto baffles 268.

The Narcissus problem mentioned above is a well-known defect in infrared systems that appears as an unwanted area on a displayed image caused when a portion of the original image forming radiation reflects from the detector then off the usual spherical warm stop surfaces and back onto the detector. Here, circular flat surface 274 obviates Narcissus radiation by diverging radiation reflected from detector 220 in directions generally away from detector 220 on its return path along paths generally toward detector 220.

The frusto-conical surface 270 of warm stop 216, which is at 60° with respect to the optical axis, operates to direct stray radiation onto baffles 268 of camera 266. As will be apparent to those skilled in the art, the angles and size of such warm stop surfaces are a function of the specific geometric relationships among relevant elements of the system, i.e., the spacings, size, and angles, between the warm stop surfaces, the cold stop, the baffles, and detector. The essential point is that the surface of warm stop be non-imaging with respect to detector 220 to eliminate or reduce Narcissus defects and other stray radiation while also directing stray radiation from sources outside the desired field of view of the system away from the detector and into the baffles where it is absorbed and rendered harmless. As those skilled in the art will further recognize, the foregoing functions may also be provided by generally shaped non-imaging surfaces that are other than of frusto-conical geometry as, for example, non-imaging Winston cusps or multi-faceted surfaces.

Thus, in this system, a warm stop of novel design is used which permits the objective elements to be small, and hence lightweight and relatively less expensive than if larger. It also permits the camera to be used with a range of lens designs of differing focal length and field angle up to the largest field that may be accommodated by the size of the cold stop.

The foregoing arrangement, thus also allows the system to be more compact by virtue of the fact that such a warm stop can be smaller, and the camera lenses can be closer to it.

It is to be noted that the above constructional data has been optimized for image quality at 5 microns but, because of the low chromatic dispersion and flat index of refraction profile for Germanium, the image quality over the region from 2 to 14 microns will likewise be acceptable so that the inventive IR endoscope is useable over this extended range.

The rod lens design of the present invention is a departure from the usual design practice of using a right cylindrical rod with lenses cemented to or air-spaced from a rod's outboard surfaces. This was intentionally done to minimize absorptive and Fresnel reflection losses. Since the brightness of the image is a function of the optical invariant squared (neglecting absorption and scattering losses), or B (brightness) $\propto (y\theta n)^2$ where n is the index of refraction, y the height of the entering ray, and $\theta$ its entrance angle with the optical axis. If n is high, B will correspondingly be higher by the square of n. By using a very high index material such as germanium, whose index at the working wavelength is 4.0, the brightness increases by a factor of 16 compared with air. However, since Fresnel reflection losses at interfaces are dependent on index, antireflection coatings must be used wherever Fresnel losses may be introduced. On the other hand, the use of internal images reduces the occurrence of potential Fresnel reflecting interfaces compared with usual practice. Here, the number of interfaces eliminated has been estimated to be in the range of 14 to 24, a result achieved by incorporating refracting surfaces on the ends of what would otherwise be planar rod lenses. With a reflection loss of 0.5 percent per surface, the specification for this system, the throughput for 37 surfaces is 83 percent. With 14 to 24 more surfaces, the throughput would range between 74 to 77 percent. Hence, this system has between 7 to 12 percent more throughput compared with systems with more potential sources of Fresnel reflections.

In addition, the low absorption coefficient of 0.003/cm puts the transmission for approximately 375 cm of germanium at 89 percent. The absorption is given by $e^{-\alpha x}$ where x is the length and $\alpha$ is the absorption coefficient per unit length. For an $\alpha$ of 0.003 and a length of 37.5 cm for optical grade, low-absorption germanium, the transmission is thus 0.894.

Camera objective 212 balances primarily chromatic, coma, astigmatism, and distortion allowed in downstream elements and residual within itself. Since the elements of the relay sections are of high index, their surfaces are shallower radius than with lower index of refraction materials to achieve the same refractive power. Consequently, aberrations that are dependent on curvature are reduced because of this design feature while brightness is enhanced. The image quality is near diffraction limited. The f/# of this endoscope is f/5.5 which gives a diffraction limit of 66.0$\mu$ at a wavelength of 4.51$\mu$. Since the array has square pixels of 38$\mu$, this spatial resolution spans about two pixels worth of image. Thus, the limiting spatial resolution of the system is provided from the optical train, but those skilled in the art will recognize that the aperture could be made larger but with a reduction in depth of focus or field.

Another feature of the design of the example of the constructional data of the above Table II is that the objective elements in the system have not been optimized independently to provide optimally corrected images in the distal and proximal ends of the system. Instead, the corrective work has been shared by both the distal end objective and coupling lens so that the distal end objective 206 could be of simpler design, having fewer elements than if it were required to provide a fully corrected image.

The preferred embodiment of the foregoing example has only two relay sections, which gives an inverted image, but. this is easily inverted via the video system. This is optically beneficial, however, because there is no need to use an odd number of relay sections, and hence, this reduces the number of elements needed and their attendant reduction of throughput via Fresnel reflections and absorption.

Thus, a rigid all lens system that has been optimized for use at between 2–5$\mu$ has been provided. Its thermal resolution is better than 0.1° C. because of the f/5.5 aperture and camera sensitivity. The nominal working distance is 38 mm with a range of focus of 5 mm to infinity, thus making it particularly suitable for endosurgical procedures. One of the major advantages of this system is its combined spatial and thermal resolution which permits detection of smaller pathology early on. It will also be recognized that the foregoing example can readily make use of the image processing and video procedures previously described in connection with the earlier examples and may also be used with or be incorporated along with a visible endoscope. In addition, it will be recognized that the geometry of the warm stop arrangement may be appropriately scaled so that it can be used in cameras that are designed to accept a range of lenses of different focal length. Where this is contemplated, the camera cold stop is typically made large enough to accommodate the widest field of view. Thus, one may have warm stops fitted to the adapter rings in which the warm stop may be resident, and these may be easily changed with a change in coupler lens focal length.

Those skilled in the art may make other changes to the invention without departing from the scope of its teachings. Aside from medical applications, it would be possible in appropriate circumstances to use the invention for industrial applications. Moreover, it will also be appreciated by those skilled in the art that the lenses of the invention may be fabricated of other suitable IR materials such as ZnSe, ZnSu, Irtran I and II, and CaFl. Therefore, it is intended that the embodiments described herein be considered as illustrative and not be construed in a limiting sense.

What is claimed is:

1. An endoscope system for use in imaging infrared emissions from within the range including 2 to 14 microns, said system comprising:
   a refractive objective lens for forming a real image of a subject of interest in an image plane;
   at least one relay section consisting solely of refracting elements for transferring said real image to form an intermediate image in a conjugate plane located near the proximal end of said system, said refractive objective lens and said relay section sharing at least one unitary element in common which performs both objective lens and relay functions;
   a refracting coupling lens for forming a final image of said intermediate image in a detector plane located at the proximal end of said system; and
   a warm stop located near the proximal end of said system, said warm stop having an aperture therethrough that defines the aperture stop of said system, said warm stop including a selectively shaped surface that is non-imaging with respect to said detector plane and structured to direct stray and a portion of Narcissus radiation away from the system detector with the remaining Narcissus radiation being non-imaging with respect to the detector.

2. The system of claim 1 wherein all of the elements of said system are selected from the group consisting of germanium and AMTIR-1.

3. The system of claim 1 wherein said non-imaging surface comprises a planar annulus and frustro-conical annulus connected to one another.

4. The system of claim 3 wherein said planar annulus includes portions that define said aperture of said warm stop and directs and operates primarily on Narcissus type radiation and said frusto-conical annulus operates to direct unwanted radiation away from the system detector.

5. The system of claim 1 wherein said warm stop is constructed of low-emissivity specular material.

6. The system of claim 1 further including an infrared imaging detector proximate said detector plane.

7. The system of claim 6 wherein said infrared imaging detector is an array detector comprising indium antimonide.

8. The system of claim 1 further including an infrared video camera having a cooled infrared imaging detector located at said detector plane.

9. The system of claim 8 further including a coupling adapter for mechanically linking said camera to the proximal end of said coupler lens, said coupling adapter including a warm stop for said system.

10. The system of claim 8 wherein said camera generates standard video signals wherein different levels of infrared radiation imaged by said system are encoded as different levels of a preselected gamut of colors.

11. The system of claim 10 wherein said colors comprise at least two different colors.

12. The system of claim 11 wherein said colors are monochromatic over a predetermined tonal scale.

13. The system of claim 1 having an f/number of substantially 5.5.

14. The system of claim 13 having a semi-field angle of 40°.

15. The system of claim 1 having an overall length of 375 mm and an endoscope diameter of 10 mm.

16. The system of claim 15 consisting essentially of two relay sections.

17. The system of claim 1 wherein said real image and at least one intermediate image formed by said relay system are formed inside of optical elements comprising said system.

18. An endoscope system for use in imaging infrared emissions from within the range including 2 to 14 microns within a intended field of view, said system comprising:
   a refractive objective lens for forming a real image of a subject of interest in an image plane;
   least one relay section for transferring said real image to form an intermediate image in a conjugate plane located near the proximal end of system;
   a refracting coupling lens for forming a final image of said intermediate image in a detector plane located at the proximal end of said system;
   an infrared imaging detector located in said detector plane to receive said real image;
   a cold stop located intermediate said detector and said refracting coupling lens; and
   a warm stop located intermediate said cold stop and said refracting coupling lens, said warm stop having portions defining the aperture stop of said system and low-emissivity reflecting surfaces facing said detector and structured to be non-imaging with respect to any unwanted radiation outside of said system's intended field of view.

19. The system of claim 18 wherein all of the elements of said system are selected from the group consisting of germanium and AMTIR-1.

20. The system of claim 18 wherein said non-imaging reflecting surfaces of said warm stop comprise a planar annulus and frustro-conical annulus connected to one another.

21. The system of claim 20 wherein said planar annulus includes said portions that define said aperture of said warm stop and operates to primarily direct Narcissus type radiation away from said infrared imaging detector and said frusto-conical annulus operates to direct unwanted radiation away from said infrared imaging detector.

22. The system of claim 18 wherein said relay section comprises all refractive optical elements.

23. The system of claim 18 wherein said infrared imaging detector is an array detector comprising indium antimonide.

24. The system of claim 18 further including an infrared video camera which includes said infrared imaging detector located at said detector plane.

25. The system of claim 24 further including a coupling adapter for mechanically linking said camera to the proximal end of said coupler lens, said coupling adapter including said warm stop for said system.

26. The system of claim 24 wherein said camera generates standard video signals wherein different levels of infrared radiation imaged by said system are encoded as different levels of a preselected gamut of colors.

27. The system of claim 26 wherein said colors comprise at least two different colors.

28. The system of claim 27 wherein said colors are monochromatic over a predetermined tonal scale.

* * * * *